(12) United States Patent
Kozel et al.

(10) Patent No.: US 9,775,909 B2
(45) Date of Patent: *Oct. 3, 2017

(54) PEROXIDE DISPERSIONS

(71) Applicant: Arkema Inc., King of Prussia, PA (US)

(72) Inventors: Thomas H. Kozel, Pottstown, PA (US); Joseph M. Gravelle, Spring City, PA (US); Timothy Belford, Stokesdale, NC (US); Tomas Salvador, Sugar Land, TX (US)

(73) Assignee: Arkema Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/407,476

(22) PCT Filed: Mar. 1, 2013

(86) PCT No.: PCT/US2013/028492
§ 371 (c)(1),
(2) Date: Dec. 12, 2014

(87) PCT Pub. No.: WO2013/187949
PCT Pub. Date: Dec. 19, 2013

(65) Prior Publication Data
US 2015/0165043 A1    Jun. 18, 2015

Related U.S. Application Data

(60) Provisional application No. 61/660,148, filed on Jun. 15, 2012.

(51) Int. Cl.
*A61K 47/34* (2017.01)
*A23L 5/49* (2016.01)
*C11C 3/02* (2006.01)
*A61K 31/327* (2006.01)
*A61K 9/14* (2006.01)
*A61K 47/08* (2006.01)

(52) U.S. Cl.
CPC ............ *A61K 47/34* (2013.01); *A23L 5/49* (2016.08); *A61K 9/14* (2013.01); *A61K 9/145* (2013.01); *A61K 31/327* (2013.01); *A61K 47/08* (2013.01); *C11C 3/02* (2013.01); *A23V 2002/00* (2013.01)

(58) Field of Classification Search
None
See application file for complete search history.

(56) References Cited

U.S. PATENT DOCUMENTS

| | | |
|---|---|---|
| 2,684,971 A | 7/1954 | Alsop |
| 3,397,245 A | 8/1968 | Appell |
| 3,507,800 A | 4/1970 | Leveskis |
| 3,825,509 A | 7/1974 | Miller |
| 3,843,801 A | 10/1974 | Efthymiou |
| 4,039,475 A | 8/1977 | Oosterwijk et al. |
| 4,092,470 A | 5/1978 | Oosterwijk et al. |
| 4,440,885 A | 4/1984 | Tamosauskas |
| 4,734,135 A | 3/1988 | Satomi et al. |
| 4,842,765 A | 6/1989 | Satomi |
| 5,110,495 A * | 5/1992 | Self ............ C08F 4/32 252/186.26 |
| 5,300,600 A | 4/1994 | Bock et al. |
| 5,478,490 A | 12/1995 | Russo et al. |
| 5,690,856 A | 11/1997 | Milleville et al. |
| 5,871,800 A | 2/1999 | George et al. |
| 5,914,301 A | 6/1999 | Hsu et al. |
| 6,113,921 A * | 9/2000 | Friedman et al. ............ 424/400 |
| 6,120,820 A | 9/2000 | Brody et al. |
| 8,697,130 B1 | 4/2014 | Gerlach et al. |
| 2004/0101566 A1 | 5/2004 | Cooper et al. |
| 2004/0185066 A1 | 9/2004 | Uang et al. |
| 2009/0215629 A1 | 8/2009 | Bevinakatti et al. |
| 2010/0261795 A1 | 10/2010 | Buzot |
| 2011/0086959 A1 | 4/2011 | Kozel et al. |
| 2012/0010352 A1 | 1/2012 | O |
| 2012/0157366 A1 | 6/2012 | Anim-Danso et al. |
| 2012/0196843 A1 | 8/2012 | Fares et al. |
| 2013/0143786 A1 | 6/2013 | Zhu et al. |

FOREIGN PATENT DOCUMENTS

| | | |
|---|---|---|
| GB | 238544 | 4/1930 |
| GB | 1156573 | 7/1969 |
| RU | 2 285 011 C2 | 10/2006 |
| WO | WO 2007/005471 A2 | 1/2007 |
| WO | WO 2012/170866 A1 | 2/2012 |

OTHER PUBLICATIONS

Cyber Lipid, "Polyglyceryl Esters," <http://www.cyberlipid.org/glycer/glyc0013.htm>, published Apr. 8, 2010, p. 1-2.*
Lonza, "Polyaldo 10-1-CC-KFG (Non GMO)," <http://bio.lonza.com/uploads/tx_mwaxmarketingmaterial/Lonza_ProductDataSheets_Polyaldo_10-1-CC_KFG_NON_GMO_PDS.pdf>, Revised May 3, 2010, p. 1-2.*
Drugs.com, "Potassium Citrate," Drug Information Online, <http://www.drugs.com/cdi/potassium-citrate.html>, published Jul. 14, 2010, p. 1-4.*
RxMed, "Calcium Chloride Injection USP," <http://www.rxmed.com/b.main/b2.pharmaceutical/b2.1.monographs/CPS-%20Monographs/CPS-%20(General%20Monographs-%20C)/CALCIUM%20CHLORIDE%20INJECTION%20USP.html>, published Jul. 4, 2008, p. 1-4.*
S. Kuramoto & J.J. Jezeski, Department of Dairy Husbandry, Unv. Minnesota, St. Paul—"Some Factors Affecting the Action of Benzoyl Peroxide in the Bleaching of Milk and Cream for Blue Cheese Manufacture" Jun. 4, 1954; pp. 1241-1246.
Yehia El-Samragy, Chemical and Technical Assessment (CTA) FOA 2004 "Benzoyl Peroxide" pp. 1(6)-6 (6).
Listiyani et al; American Dairy Science Association 2012, "Effect of Temperature and Bleaching Agent on Bleaching of Liquid Cheddar Whey" pp. 36-49.

* cited by examiner

Primary Examiner — Tracy Vivlemore
Assistant Examiner — Monica Shin
(74) Attorney, Agent, or Firm — Lynn B. Morreale

(57) ABSTRACT

The viscosity of aqueous dispersions of normally solid organic peroxides may be advantageously lowered through the use of surfactants which are polyglyceryl esters of C6-C12 fatty acids. The reduction in viscosity facilitates milling the peroxides to reduce particle size and also provides dispersions of small particle size peroxides which may be readily poured or pumped.

12 Claims, No Drawings

PEROXIDE DISPERSIONS

CROSS-REFERENCE TO RELATED APPLICATIONS

This application is a national stage application under 35 U.S.C. §371 of PCT/US2013/028492, filed Mar. 1, 2013, which claims benefit to U.S. application Ser. No. 61/660,148, filed on Jun. 15, 2012.

FIELD OF INVENTION

The present invention relates to aqueous dispersions of normally solid organic peroxides. The dispersions are pastes or liquids which contain high concentrations of the peroxide, wherein the peroxide is present in the form of small particles (e.g., less than 10 μm diameter on average). The pastes are shear thinning or sufficiently flowable so as to be pumpable/pourable, which makes their handling and use easier.

BACKGROUND

Peroxides have, as a general property, a tendency to be flammable and explosive with some peroxides exhibiting such properties to a greater extent than others. For example, benzoyl peroxide may decompose when dry due to shock, friction, or static electricity. This property carries with it the hazards to the users of these materials as well as to the manufacturers and intermediate handlers thereof. Accordingly, it has long been an object to provide flame resistant organic peroxide compositions.

The safety and end-use advantage provided by water-soluble or water-dispersible peroxides has been recognized. However, many peroxides of commercial interest are water insoluble. Moreover, dispersions containing relatively high concentrations of water insoluble, solid peroxides are typically quite viscous and therefore difficult to handle and process. This problem is particularly aggravated as the particle size of the peroxide is reduced. For example, when milling a peroxide in water to reduce its particle size below 10 μm, the aqueous dispersion often forms a very thick paste. Further milling becomes quite difficult unless milling is discontinued for a period of time to permit the dispersion to "relax" and soften to an extent where milling again becomes feasible. These difficulties significantly lengthen the period of time necessary to achieve a desired small particle size. As there are many end use applications for water insoluble peroxides where smaller particle size will be advantageous, there remains a need for highly concentrated aqueous dispersions of small particle size peroxides which are capable of being handled by pumping and/or pouring as well as methods by which such aqueous dispersions may be conveniently and efficiently prepared.

BRIEF SUMMARY OF THE INVENTION

The present invention provides an aqueous dispersion comprising a) about 40% by weight or more of a water-insoluble, solid organic peroxide having an average particle size of less than 10 μm and b) a surfactant which is a polyglyceryl ester of one or more C6-C18 fatty acids. In another aspect, the invention provides a process for making such an aqueous dispersion, comprising milling an organic peroxide having an average particle size of greater than 10 μm in water in the presence of a surfactant which is a polyglyceryl ester of one or more C6-C18 fatty acids. Using such a surfactant helps to reduce the viscosity of the aqueous dispersion during processing.

DESCRIPTION OF VARIOUS EMBODIMENTS OF THE INVENTION

Aqueous dispersions of the present invention comprise an organic peroxide which is normally solid (i.e., a solid at room temperature) and a surfactant.

Exemplary of suitable organic peroxides are aromatic diacyl peroxides, such as benzoyl peroxide, o-methylbenzoyl peroxide, o-methoxybenzoyl peroxide, o-ethoxy benzoyl peroxide, o-chlorobenzoyl peroxide and 2,4-dichlorobenzoyl peroxide; aliphatic diacyl peroxides, such as decanoyl peroxide, lauroyl peroxide and myristoyl peroxide; ketone peroxides, such as 1-hydroxy cyclohexyl peroxide and 1-hydroperoxycyclohexyl peroxide; aldehyde peroxides such as 1-hydroxy heptyl peroxide; peroxy dicarbonates such as dicetyl peroxydicarbonate, di(4-t-butylcyclohexyl) peroxydicarbonate and acylperoxy alkylcarbonates, such as acetyl peroxy stearyl carbonate and the like and mixtures thereof. Other organic peroxides which are normally solid at room temperature and substantially insoluble in water may also be employed. The starting organic peroxide may be obtained by any suitable method and may be in solid (dry) form or in the form of a mixture with water. As will be described in more detail hereafter, the organic peroxide typically has a relatively large particle size to begin with (e.g., greater than 10 μm) and then is reduced in size through any suitable procedure in the presence of the surfactant and water to provide the aqueous dispersions of the invention.

The present aqueous dispersions comprise about 35 percent or more by weight of an organic peroxide. One of the features of the present invention is that it enables the preparation of aqueous dispersions containing about 35 or more percent by weight of organic peroxide, wherein the dispersions are pumpable or pourable because they are shear thinning or flowable liquids. Heretofore it has been difficult to make pumpable dispersions containing about 35 or more percent by weight organic peroxide. In this description, shear thinning means that viscosity drops as the shear rate increases. Thus, the viscosity of the peroxide dispersions of the present invention will drop as the dispersion is stirred or mixed and it becomes pourable or pumpable easing use. In some embodiments of the invention, the aqueous dispersion is sufficiently fluid such that it is capable of being poured even without being subjected to stirring or mixing. The concentration of the peroxide in the aqueous dispersion may be adjusted as may be desired or needed, but typically the organic peroxide concentration is at least about 30 weight percent but not greater than about 75 weight percent, or between about 35 to 60 weight percent, or between about 37 to not greater than about 53 weight percent, or between about 37 to about 42 weight percent.

Sufficient water is present to provide an aqueous dispersion, with water acting as a liquid matrix within which particles of the organic peroxide are dispersed. Typically, the water content of the aqueous dispersion is from about 25 to 70 weight percent, from about 40 to 65 weight percent, from about 42 to about 63 weight percent, or from about 53 to about 63 weight percent, or from about 58 weight percent to about 63 weight percent. The pH of the water may be adjusted as may be desired or needed by the addition of one or more pH adjusting agents such as bases, acids, buffers and the like. Soluble species such as salts may also be present.

Besides the water and organic peroxide, the composition of the present invention also comprises one or more surfactants. In one embodiment, the surfactant is a pharmaceutically acceptable surfactant. A pharmaceutically acceptable surfactant refers to a surfactant that does not cause significant irritation to an organism and does not abrogate the biological activity and properties of an administered compound that the dispersion of the present invention is combined with. In another embodiment, the surfactant is a food grade surfactant. A food grade surfactant refers to a surfactant which is permitted by regulation to be present in a foodstuff, at least up to certain levels. The surfactant used may be both a pharmaceutically acceptable surfactant and a food grade surfactant.

It has now been surprisingly discovered that polyglyceryl esters of one or more C6-C18 fatty acids, or preferably polyglyceryl esters of one or more C6-C12 fatty acids, or preferably polyglyceryl esters of one or more C8-C12 fatty acids, are particularly effective in providing dispersions which remain free flowing liquids during the milling process used to reduce the average particle size of the organic peroxide to below 10 μm and preferably above 2 μm. That is, the use of other types of surfactants leads to the formation of very thick pastes during milling that significantly increases the time needed to achieve a particular desired small particle size. The present invention thus provides substantial improvement in processing efficiency.

Polyglyceryl esters of fatty acids are also referred to in the art as "polyglycerol esters of fatty acids" and "polyglycerol fatty acid esters." They may be described as mixed partial esters formed by reacting polymerized glycerols with edible fats, oil or fatty acids. Commercial surfactants which are polyglyceryl esters of fatty acids may include minor amounts of mono-, di- and tri-glycerides, free glycerol and polyglycerols, free fatty acids and/or salts of free fatty acids. The degree of polymerization of the polyglyceryl component may vary. In various embodiments of the present invention, the polyglyceryl segment of the surfactant may contain at least 2, 3, 4, 5, 6, 7, 8 or 9 and/or not more than 20, 19, 18, 17, 16, 15, 14, 13, 12 or 11 glyceryl repeating units on average per molecule. In one particular embodiment, about 10 glyceryl repeating units per molecule on average are present.

It has been unexpectedly discovered that using polyglyceryls esterified with relatively short chain fatty acids as surfactants in a process wherein a relatively large particle size organic peroxide (e.g., having an average particle size greater than 10 μm) is milled in water to a smaller particle size (e.g., less than 10 μm or less than 5 μm average particle size and in some embodiments preferably greater than 2 μm average particle size) helps to lower viscosity during such a milling process. The resulting aqueous dispersion is shear thinning. The fatty acids used to esterify the polyglyceryl thus are predominantly C6-C18 fatty acids, or C6-C12 fatty acids, or C8-C12 fatty acids (i.e., fatty acids containing 6 to 18, or 6 to 12, or 8 to 12 carbon atoms per molecule), although minor amounts of shorter and/or longer chain fatty acids may also be present in the esterified polyglyceryl. For example, in various embodiments of the invention, at least 50, at least 60, at least 70, at least 80, at least 90 or essentially all of the fatty acid moieties present in the surfactant are C6-C18 or C6-C12 fatty acid moieties. Mixtures of different C6-C18, or C6-12, C8-C12, fatty acid moieties may be present. The fatty acid moieties may be straight chain or branched, saturated or unsaturated. Typically, the fatty acid moieties are monocarboxylate moieties corresponding to the general structure —OC(=O)R, where R is a C5-C11 alkyl group. In one embodiment, the fatty acid moieties present in the surfactant are predominantly saturated, such that the iodine value of the surfactant is less than 10 or less than 5. Examples of suitable C6-C18 fatty acids include, but are not limited to, hexanoic acid (also known as caproic acid), octanoic acid (also known as caprylic acid), decanoic acid (also known as capric acid) and dodecanoic acid (also known as lauric acid), tetradecanoic acid (also known as myristic acid) hexadecanoic acid (also known palmitic), octadecanoic (also known as sterearic acid) and mixtures thereof. In one embodiment, the C6-C12 fatty acid is a mixture of octanoic acid and decanoic acid (with other fatty acids possibly being present in minor amounts).

Typically, the polyglyceryl is partially esterified with fatty acid moieties, with one or more hydroxyl groups remaining unesterified. For example, the surfactant may contain an average of 1 to 3 fatty acid moieties per molecule. In certain embodiments, from about 25% to about 60%, or from about 30% to about 50%, of the available hydroxyl groups in the polyglyceryl are esterified with fatty acid moieties.

The surfactant may correspond to the general structure (I):

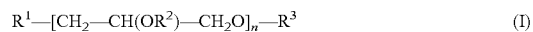

$$R^1-[CH_2-CH(OR^2)-CH_2O]_n-R^3 \qquad (I)$$

wherein the average value of n is from about 6 to about 14 and $R^1$, $R^2$ and $R^3$ are each independently a C6-C18 fatty acid moiety or hydrogen, provided that at least one of $R^1$, $R^2$ or $R^3$ is a C6-C18 fatty acid moiety. In one embodiment, at least one of $R^1$, $R^2$ or $R^3$ is hydrogen. Although structure (I) shows the glyceryl repeating units arranged in a linear fashion, it is understood that the formula also encompasses polyglyceryls which are branched.

Exemplary surfactants useful in the present invention include, but are not limited to, polyglyceryl-10 caprylate/caprate, polyglyceryl-10 caprylate, polyglyceryl-10 caprate, polyglyceryl-10 laurate, as well as analogous substances where the polyglyceryl component contains an average of 8, 9, 11 or 12 glycerol repeating units per molecule. Polyglyceryl esters of C6-C18 fatty acids and polyglyceryl esters of C6-C12 fatty acids suitable for use as surfactants in the present invention are available commercially from various suppliers, such as Lonza.

In various aspects of the invention, the surfactant may have an HLB value of at least 12, 13, or 14 and/or an HLB value of not more than 18, 17 or 16. For example, the HLB value of the surfactant may be 12-18 or 14-16.

In one embodiment of the invention, the only type of surfactant present in the aqueous dispersion is a polyglyceryl ester of C6-C18 or C6-C12 fatty acids or a mixture of such surfactants. In other embodiments, such polyglyceryl esters represent at least 50, 60, 70, 80, 90 or 95% by weight of the total amount of surfactant present.

Surfactant may be combined with water and the organic peroxide in an amount effective to reduce the viscosity of the aqueous dispersion during milling of the organic peroxide. Typically, the concentration of surfactant in the aqueous dispersion is at least 0.1 weight % but no greater than 2.0 weight %.

Other components may be present in the aqueous dispersion in addition to water, surfactant and organic peroxide. For example, to assist in maintaining the product as a stable, homogeneous dispersion and inhibit settling out of the particles of organic peroxide, one or more gelling agents may be incorporated in the aqueous dispersion. A gelling agent is a substance capable of forming a gel when placed in water. Macromolecular gelling agents are particularly useful in the present invention, especially macromolecular gelling agents of natural origin such as certain polysaccharides. Suitable macromolecular gelling agents include, but are not limited to, alginates (salts of alginic acid), carrageenans, gellan gum, guar gum pectic substances (e.g., pectic acid, pectin, pectate), and xanthan gum. The gelling agent may be selected such that it is suitable for inclusion in a food or pharmaceutical product. In one embodiment, the gelling agent is capable of being further gelled through crosslinking. For example, a macromolecular gelling agent may contain one or more different types of functional groups along its backbone or pendent to the backbone which are capable of interacting or reacting with a crosslinking agent. Such functional groups may be carboxylic acid groups, sulfonic acid groups or salts thereof (carboxylates, sulfates), for example. Suitable crosslinking agents may include species providing polyvalent cations (e.g., divalent and trivalent cations). Exemplary polyvalent cations include aluminum (3+), barium(2+), calcium(2+), copper(2+), iron(2+), strontium(2+), and zinc(2+). The cations may be supplied in the form of food-safe and/or pharmaceutical-safe salts. Specific examples of suitable salts useful as crosslinking agents include the following, including their hydrates, and mixtures thereof: calcium carbonate, calcium chloride, calcium disodium edetate, calcium lactate, calcium nitrate, calcium oxalate, calcium sulfate, dicalcium phosphate, tricalcium citrate, tricalcium phosphate, and the corresponding barium, copper, strontium, and zinc analogues thereof. The amounts of macromolecular gelling agent and crosslinking agent may be varied as desired. The gelling agent may be utilized in an amount effective to reduce the tendency of the particulate organic peroxide to settle out of the aqueous dispersion over time.

In various embodiments, the aqueous dispersion contains at least 0.25 weight % or at least 0.4 weight % macromolecular gelling agent. In other embodiments, the aqueous dispersion contains not more than 1.5 weight % or not more than 0.75 weight % macromolecular gelling agent. For example, the aqueous dispersion may comprise 0.25 to 1.5 weight % macromolecular gelling agent. The amount of crosslinking agent, if used, may generally be varied in accordance with how much macromolecular gelling agent is present. For example, if the concentration of macromolecular gelling agent is relatively low, the concentration of crosslinking agent may also be relatively low.

In various embodiments, the aqueous dispersion contains at least 0.1 to 3 weight % or preferably at least about 0.25 to 1 weight % base or stabilizer or buffer. Examples of suitable bases/stabilizers/buffers include sodium hydroxide, calcium hydroxide, magnesium hydroxide, sodium bicarbonate, potassium phosphate (mono and dibasic salts), sodium citrate and the like.

Typical concentrations of crosslinking agent may be, for example, from 0.01 to 0.075 weight %.

In one embodiment, the composition of the aqueous dispersion is as follows:
 a) 37.5 to 42 weight % benzoyl peroxide having an average particle size of less than 5 µm;
 b) 53.5 to 62 weight % water;
 c) 0.25 to 1.5 weight % macromolecular gelling agent;
 d) 0.1 to 2.0 weight % polyglyceryl ester which contains a polyglycerol moiety having 8 to 12 glycerol repeating units on average which is partially esterified with a mixture of octanoic acid and decanoic acid and has an HLB value of 12-18 (e.g., polyglyceryl-10 caprylate/caprate);
 e) 0.01 to 0.05 weight % salt/crosslinking agent; and
 f) 0.25 to 1.0 weight % base/stabilizer/buffer.

The aqueous dispersion may be prepared using any process. For example, the aqueous dispersion may be prepared by milling/grinding an organic peroxide in the presence of water and surfactant until the desired particle size of the organic peroxide is achieved (e.g., less than 20 µm, or less than 15 µm, or less than 10 µm, or less than 5 µm, or between 3 to 5 µm, or 2 to 5 µm, or 1 to 5 µm, or between 3 to 10 µm, or 2 to 10 µm, or 1 to 10 µm). Particle size may be determined using ASTM UOP 856-07, Particle Size Distribution of Powder by Laser Light Scattering and are reported D50 by percent volume.

Milling may be carried out by any suitable equipment known in the art such as a rotor/stator mill, a horizontal ball mill, or, most preferably, a vertical basket mill (such as those supplied by the Hockmeyer Company). The temperature during milling should be controlled so as to avoid decomposition of the organic peroxide. Typically, the milling is conducted at temperatures of 40° C. or less. If a macromolecular gelling agent is to be included in the aqueous dispersion, it may be preferred to add it to the aqueous dispersion after the milling step. The aqueous dispersion also may be prepared using the methods known to those skilled in the art such as those disclosed in U.S. Pat. Nos. 4,039,475, 4,092,470, 4,734,135, and 4,440,885, the disclosures of which are incorporated herein in their entireties. Sonication and ultrasound applications/processes known in the art also are suitable.

Aqueous dispersions in accordance with the present invention are useful in a wide variety of end use applications where it is desired to utilize organic peroxides, including the food industry as well as the pharmaceutical industry. For example, the aqueous dispersion may be used as a food bleach or as a component of an anti-acne medication.

EXAMPLES

Example 1 (Comparative)

An aqueous dispersion is prepared having the following target composition (amounts listed are weight %):

| | |
|---|---|
| Benzoyl Peroxide | 53.3 |
| Water | 44.15 |
| Gelling agent | 0.5 |
| Decaglycerol Monooleate | 1.5 |
| Crosslinking agent | 0.05 |
| Base | 0.5 |

The surfactant used is Polyaldo 10-1-O decaglycerol monooleate (a polyglyceryl esterified with oleic acid), supplied by Lonza. The benzoyl peroxide used is a benzoyl peroxide/water mixture containing 75 weight % benzoyl peroxide (thus, the actual benzoyl peroxide content of the formulation is 40 weight %). During milling of the benzoyl peroxide to reduce the average particle size to 2 µm, the material forms a very thick paste that significantly slows the milling process. Milling must be interrupted periodically to allow the paste to "rest" and soften sufficiently so that milling can be resumed. This leads to very long milling times in order to mill the benzoyl peroxide to a 2 µm average particle size.

Example 2 (in Accordance with the Invention)

An aqueous dispersion is prepared having the following target composition (amounts listed are weight %):

| | |
|---|---|
| Benzoyl Peroxide | 53.3 |
| Water | 45.325 |
| Gelling agent of Ex. 1 | 0.25 |
| Polyglyceryl-10 Caprylate/Caprate | 0.6 |
| Crosslinking agent of Ex. 1 | 0.025 |
| Base of Ex. 1 | 0.5 |

The surfactant used is Polyaldo 10-1-CC, which is described by its supplier Lonza as "decanoic acid, mixed monoesters with decaglycerol and octanoic acid." The benzoyl peroxide used is a benzoyl peroxide/water mixture containing 75 weight % benzoyl peroxide (thus, the actual benzoyl peroxide content of the formulation is 40 weight %). Unexpectedly, improved milling efficiency is afforded by the polyglyceryl-10 caprylate/caprate surfactant as compared to the decaglycerol monooleate surfactant. The most significant improvements are that three times less surfactant is needed and the dispersion remains a free flowing liquid during the entire milling process (i.e., milling does not need to be stopped periodically). Surprisingly, the use of the polyglyceryl-10 caprylate/caprate surfactant allows a 2.5 μm average particle size to be reached twice as fast compared to when the decaglycerol monooleate is used as the surfactant, even at the reduced level of surfactant of Example 2. Since the product remains fluid throughout the entire process, temperature control is much better and the danger of decomposition significantly reduced. Due to the lower level of surfactant, less gelling agent (carrageenan) is needed in order to stabilize the dispersion. Since less carrageenan is needed, it is much easier to disperse homogeneously into the paste obtained by milling.

What is claimed is:

1. A method of making an aqueous pumpable or pourable dispersion, said aqueous pumpable or pourable dispersion comprising:
   a) about 35% by weight or more water-insoluble, solid benzoyl peroxide having an average particle size of less than 10 μm and b) 0.1 to 2 weight % surfactant which is a polyglyceryl ester of one or more C6-C12 fatty acids selected from the group consisting of octanoic acid, decanoic acid, and mixtures thereof, wherein the surfactant has an HLB value of 12 to 18,
   wherein the method comprises milling benzoyl peroxide having an average particle size of greater than 10 μm in water in the presence of the surfactant.

2. The method of claim 1, wherein the polyglyceryl ester of one or more fatty acids contains a polyglycerol moiety having 8 to 12 glycerol repeating units on average.

3. The method of claim 1, wherein the surfactant is based on a polyglyceryl having hydroxyl groups with from about 25% to about 60% of the hydroxyl groups of the polyglyceryl being esterified.

4. The method of claim 1, wherein the surfactant is a polyglyceryl-10 caprylate/caprate.

5. The method of claim 1, wherein the surfactant is a food grade surfactant and/or a pharmaceutically acceptable surfactant.

6. The method of claim 1, wherein the aqueous pumpable or pourable dispersion additionally comprises a macromolecular gelling agent.

7. The method of claim 6, herein the macromolecular gelling agent crosslinks in the presence of polyvalent cations.

8. The method of claim 6, wherein the aqueous pumpable or pourable dispersion additionally comprises base.

9. The method of claim 6, wherein the aqueous pumpable or pourable dispersion additionally comprises salt.

10. The method of claim 1, wherein the aqueous pumpable or pourable dispersion comprises benzoyl peroxide having an average particle size of less than 5 μm.

11. The method of claim 1, wherein the surfactant has structure (I):

$$R^1-[CH_2-CH(OR^2)-CH_2O]_n-R^3 \quad \text{(I)}$$

wherein the average value of n is from about 6 to about 14 and $R^1$, $R^2$ and $R^3$ are each independently a C8 or C10 fatty acid moiety or hydrogen, provided that at least one of $R^1$, $R^2$ or $R^3$ is a C8 or C10 fatty acid moiety.

12. The method of claim 1, wherein the aqueous pumpable or pourable dispersion comprises:
   (a) 37.5 to 42 weight % benzoyl peroxide having an average particle size of less than 5 μm;
   (b) 53.5 to 62 weight % water;
   (c) 0.25 to 1.5 weight % gelling agent;
   (d) 0.1 to 2.0 weight % polyglyceryl ester which contains a polyglycerol moiety having 8 to 12 glycerol repeating units on average which is partially esterified with a mixture of octanoic acid and decanoic acid and has an HLB value of 12-18;
   (e) 0.01 to 0.05 weight % crosslinking agent; and
   (f) 0.25 to 1.0 weight % base.

* * * * *